Nov. 20, 1973
Plant Pat. 3,411
C. F. ZAIGER
PEACH TREE
Filed Feb. 24, 1972
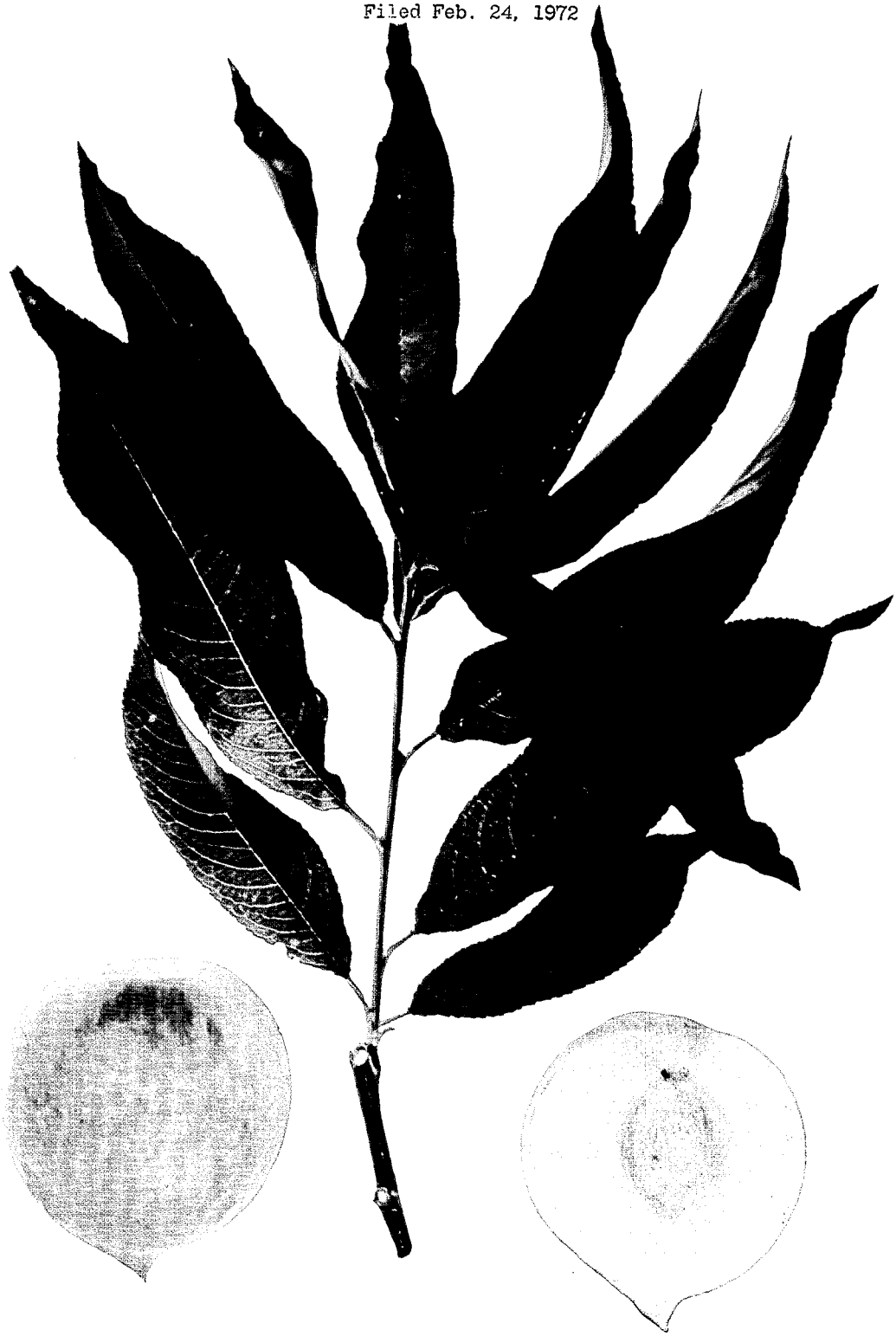

United States Patent Office

Plant Pat. 3,411
Patented Nov. 20, 1973

3,411
PEACH TREE
Chris Floyd Zaiger, 537 Rosemore Ave.,
Modesto, Calif. 95351
Filed Feb. 24, 1972, Ser. No. 229,218
Int. Cl. A01h 5/03
U.S. Cl. Plt.—43 1 Claim

ABSTRACT OF THE DISCLOSURE

A variety of peach tree which is of medium-to-large size, vigorous, medium dense, and medium upright in growth; the tree being a productive and regular bearer of medium-to-large size, early ripening, clingstone fruit having firm, yellow flesh, and yellow skin substantially overspread with red.

*Origin of the variety*

The present variety of peach tree was discovered by me growing as a bud sport on a Royal Gold (U.S. Plant Pat. No. 2,663) peach tree in my experimental orchard located in Modesto, Stanislaus County, Calif. Subsequent to recognition by me of the novel characteristics—which will hereinafter appear—of said bud sport, I propagated the variety in anticipation of ultimate introduction to the trade and to meet an existing demand for a peach tree so characterized.

*Asexual reproduction of the variety*

The present variety of peach tree was asexually reproduced by me—in my said experimental orchard—by budding, and, in maturity, such reproductions ran true—in all respects—to the orginial bud sport.

*Summary of the variety*

The present variety of peach tree is of medium-to-large size, vigorous, medium dense, upright in growth, and a productive and regular bearer of medium-to-large size, early ripening, clingstone fruit having firm, yellow flesh, and yellow skin overspread with a high degree of red; the fruit ripening, and being in harvest, ten to fourteen days earlier than the Royal Gold.

The present variety of peach tree is further characterized by fruit whose flesh has a slightly more acid flavor, and a greater degree or depth of yellow color in maturity, than the Royal Gold.

Additionally, while the fruit of the present variety is characteristically of clingstone type, some areas of the pit may frequently be free of the flesh when the fruit is fully ripe.

*Brief description of the drawing*

The drawing is an illustration, by photographic reproduction in color, of a twig with leaves, one whole fruit, and a cut fruit half with the stone remaining in place therein.

*Description of the variety*

The botanical details of this new and distinct variety of peach tree—with color definitions (except those in common color terms) referenced to Reinhold Color Atlas by A. Korneruf and J. H. Wanscher—are as follows:

Tree:
- *Size.*—Medium to large.
- *Vigor.*—Vigorous.
- *Growth.*—Medium upright.
- *Density.*—Medium dense.

- *Shape.*—Normally pruned to vase form.
- *Production.*—Productive.
- *Bearing.*—Regular.

Trunk:
- *Size.*—Medium stocky.
- *Texture.*—Shaggy.

Branches:
- *Size.*—Medium stocky.
- *Texture.*—Smooth to medium rough.
- *Color.*—*New growth:* Reddish brown. *Old growth:* Brown to grayish. *Lenticels.*—*Number:* Medium.

Leaves:
- *Size.*—Medium. Average mature length—5" to 6½". Average mature width—1½".
- *Form.*—Lanceolate, acutely pointed.
- *Texture.*—Smooth.
- *Petiole.*—Medium length, medium thickness.
- *Glands.*—Average number—4, opposite, medium size, globose, positioned on lower part of leaf blade and upper part of petiole, yellowish green.
- *Margin.*—Crenate.
- *Color.*—Top side—Medium green (28–F–8); under side—Lighter green (29–E–8); heavy midrib on under side—Yellowish-green (30–C–8).

Flower buds:
- *Size.*—Medium.
- *Length.*—Short.
- *Form.*—Plump, free.
- *Pubescence.*—Pubescent.

Flowers:
- *Blooming period.*—Date of first bloom, Mar. 4, 1971. Date of full bloom, Mar. 12, 1971.
- *Size.*—Medium.
- *Pollen.*—Present.
- *Color.*—Pink.

Fruit:
- *Maturity when described.*—Hard ripe.
- *Date of first picking.*—May 10, 1971.
- *Date of last picking.*—May 19, 1971.
- *Size.*—Medium to large. Average diameter axially—2⅛" to 2¾". Average transversely in suture plane—2¾".
- *Form.*—Globose. Slightly flattened at stem end in larger sizes. Some oblong in smaller sizes.
- *Suture.*—Shallow and nearly disappears at maturity.
- *Ventral surface.*—Rounded and only very slightly lipped.
- *Cavity.*—Rounded. Average depth—⅜". Average breadth—⅞".
- *Base.*—Retuse.
- *Apex.*—Varied from slightly retuse to small sharply pointed pistil point.

Skin:
- *Thickness.*—Medium.
- *Texture.*—Medium tender.
- *Tenacity.*—Tenacious to flesh when firm ripe; free when soft ripe.
- *Tendency to crack.*—None.
- *Down.*—Moderate. Medium length.
- *Color.*—Bright yellow (4–A–8) shading to (4–B–8) undercolor. Red blush covering most of the surface of the peach, shading from a light red (8–A–8) to a darker red (8–B–8).

Flesh:

*Amygdalin.*—Undetected.
*Juice.*—Abundant, rich.
*Texture.*—Firm.
*Fibers.*—Few, tender.
*Ripens.*—Evenly.
*Flavor.*—Very slightly acid.
*Aroma.*—Slightly fragrant.
*Eating quality.*—Good.
*Color.*—Yellowish orange (4–A–8) to golden yellow (5–A–7).

Stone:

*Type.*—Clingstone.
*Size.*—Medium. Average length—1¼". Average width—¾". Average thickness—½".
*Fibers.* —Few on grooved side.
*Form.*—Obovate. Tip—acuminate.
*Base.*—Long, tapering.
*Hilum.*—Oval, shallow.
*Apex.*—Acuminate.
*Sides.*—Irregularly furrowed toward apex. Pitted toward base.
*Tendency to split.*—Slight but noticeable.
*Color.*—Light tan.

Use:

Culinary
Dessert
Market—local and long distance shipping.

Keeping quality: Good.
Shipping quality: Good.

The peach tree and its fruit described may vary in slight detail due to climatic and soil conditions under which the variety may be grown; the present description being of the variety as grown in the Central Valley of California.

the variety may be grown; the present description being of the variety as grown in the Central Valley of Calif.

I claim:

1. A new and distinct variety of peach tree, substantially as illustrated and described, bearing medium-to-large, firm, yellow flesh, clingstone fruit—with a high degree of exterior red color—characterized as to novelty, when compared with the Royal Gold, by ripening ten to fourteen days earlier.

No references cited.

ROBERT E. BAGWILL, Primary Examiner